United States Patent [19]
Keaveney et al.

[11] Patent Number: 5,938,018
[45] Date of Patent: Aug. 17, 1999

[54] CIGARETTE OR TOBACCO PACKAGE WITH RE-USABLE AROMA RELEASANT FOR MULTIPLE PACKAGE OPENINGS

[75] Inventors: Benedict Keaveney, Rexdale; David R.E. Thomas, Toronto, both of Canada

[73] Assignee: Rothmans, Benson & Hedges Inc., Ontario, Canada

[21] Appl. No.: 09/060,404

[22] Filed: Apr. 15, 1998

[30] Foreign Application Priority Data

Apr. 15, 1997 [CA] Canada ................................... 2202717

[51] Int. Cl.⁶ .................................................. B65D 85/10
[52] U.S. Cl. ............................ 206/261; 206/265; 206/268
[58] Field of Search .................................. 206/216, 242, 206/264, 265, 270, 271, 273, 261

[56] References Cited

U.S. PATENT DOCUMENTS

| | | | |
|---|---|---|---|
| 3,685,734 | 8/1972 | Paclorek et al. | 239/56 |
| 4,717,017 | 1/1988 | Sprinkel et al. | 206/264 |
| 4,720,423 | 1/1988 | Fraser | 428/313.5 |
| 5,249,676 | 10/1993 | Ashcraft et al. | 206/264 |
| 5,333,729 | 8/1994 | Wolfe | 206/268 |

*Primary Examiner*—Jim Foster
*Attorney, Agent, or Firm*—Banner & Witcoff, Ltd.

[57] ABSTRACT

A re-usable aroma releasant is provided on a package of tobacco product such as cigarettes, pipe tobacco, fine cut tobacco and the like. The aroma releasant is activated to release aroma every time the package is opened. The packages comprises a tobacco product containment portion and a tobacco product containment closure portion. The closure portion is removed from the containment portion to gain access to the tobacco product. The aroma releasant may have a peel seal connecting the containment portion and the closure portion. The peel seal seals the aroma in the substrate reservoir provided on the package. The peel seal is peeled from the substrate reservoir to permit opening of the package and simultaneously releasing aroma from the reservoir. The peel seal reseals the reservoir on closure of the package. A re-usable aroma releasant is provided where every time the smoker opens the package, fresh aroma is released. Suitable aromas include, essence of tobacco, coffee, menthol or other pleasant aromas associated with tobacco smoking.

19 Claims, 5 Drawing Sheets

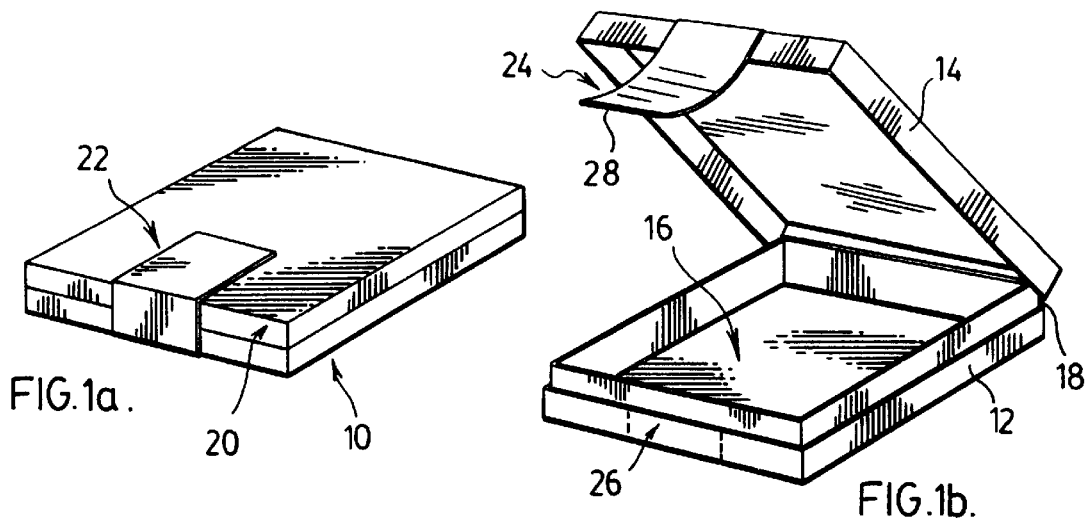
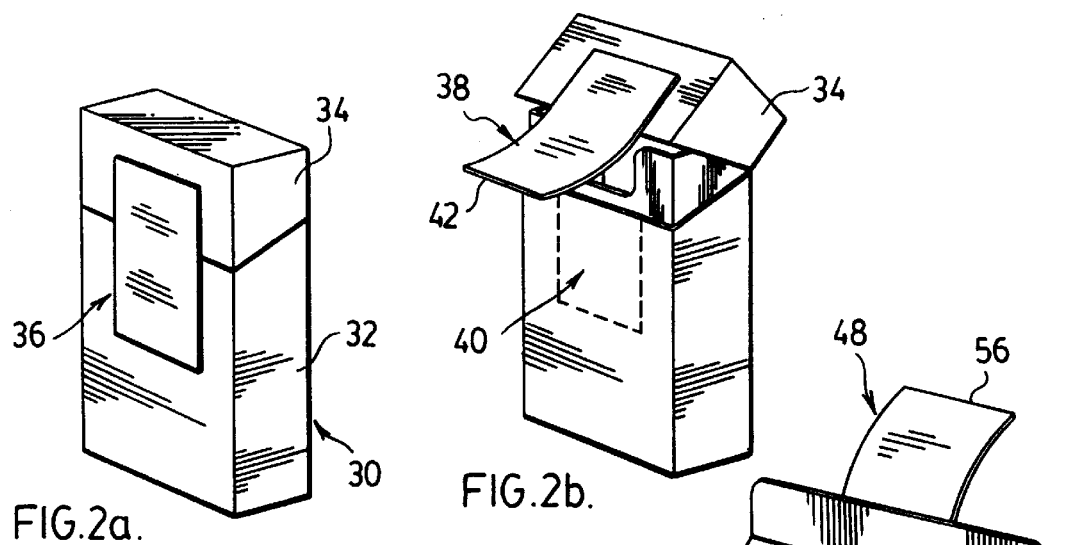
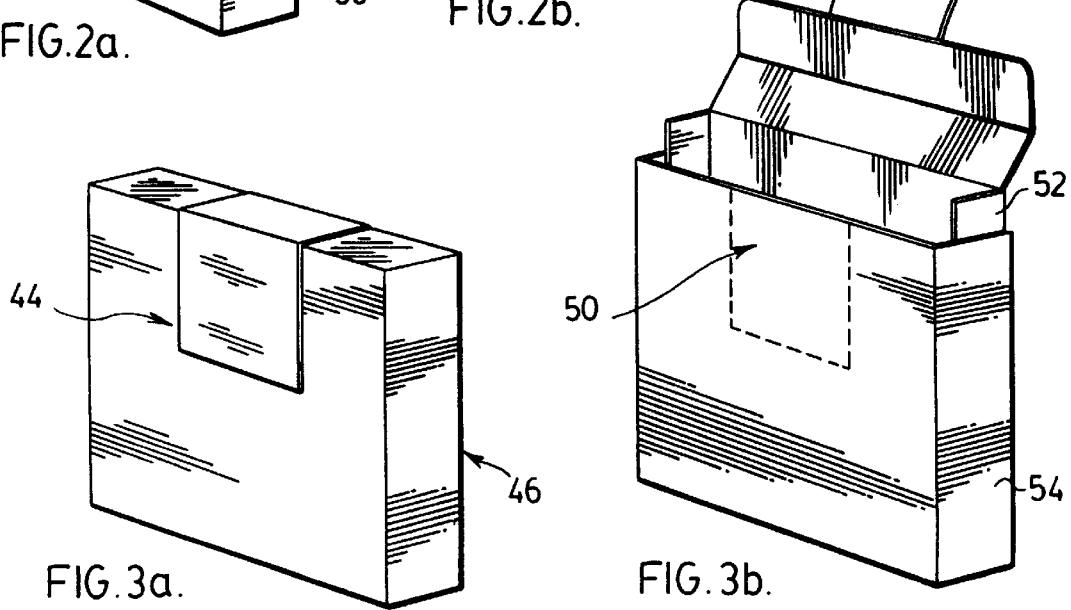

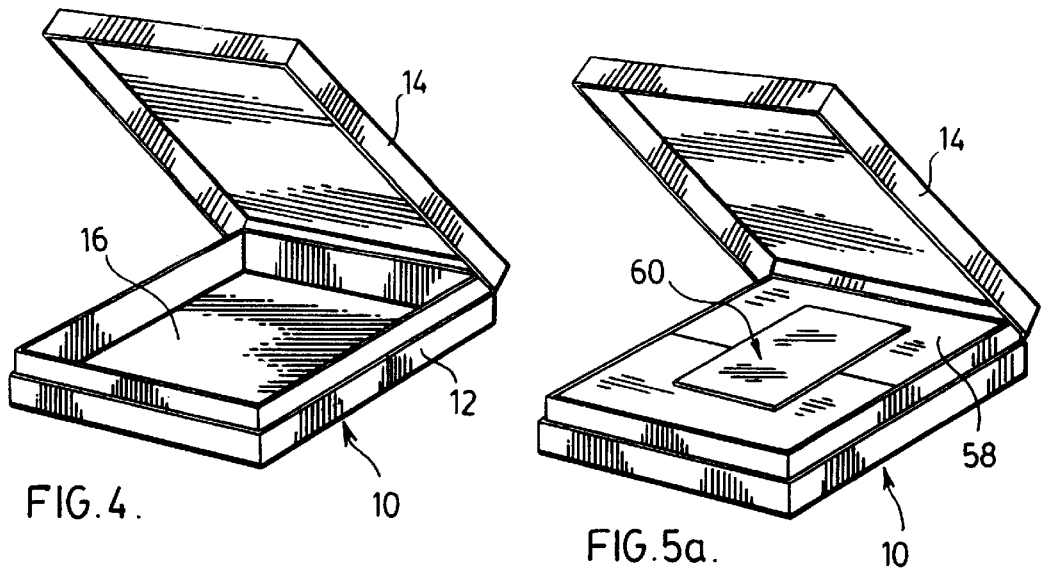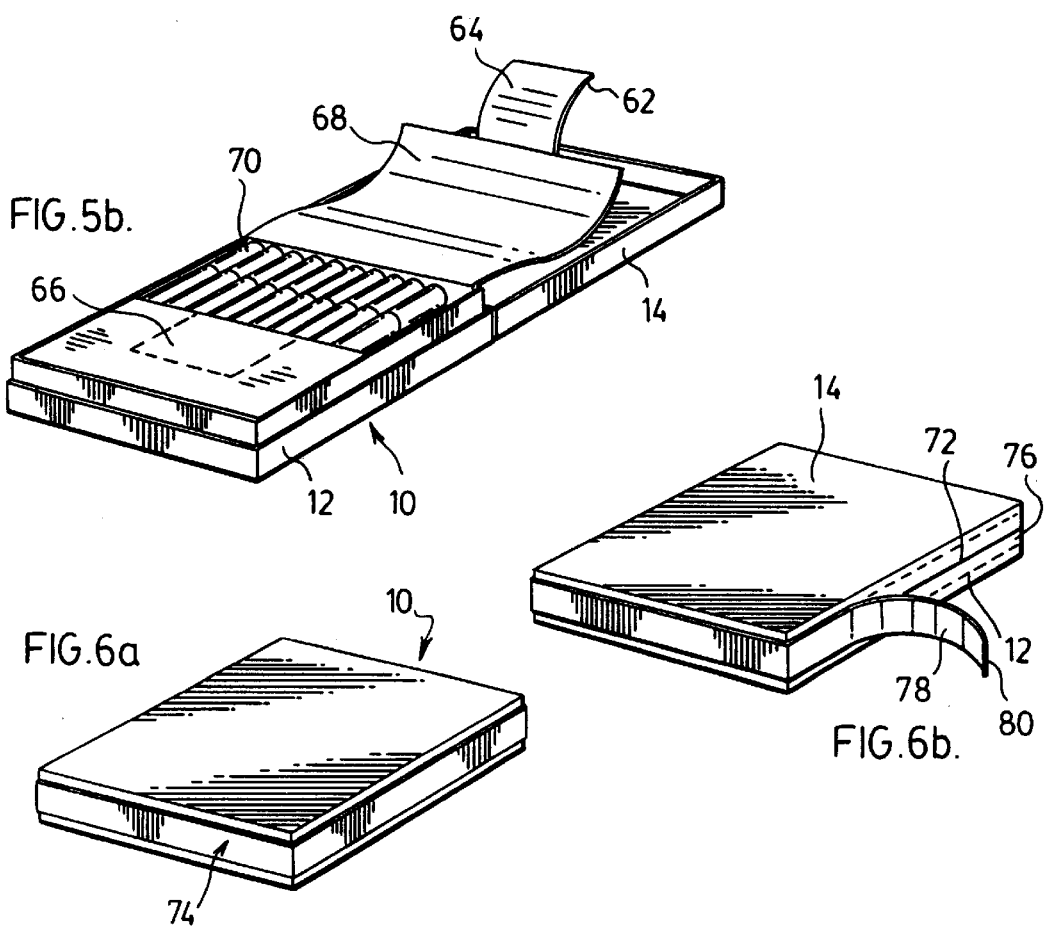

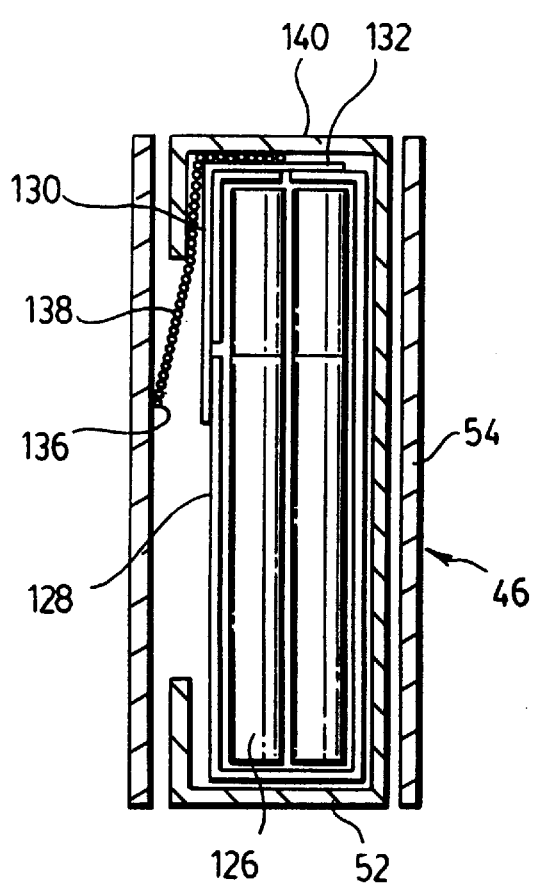
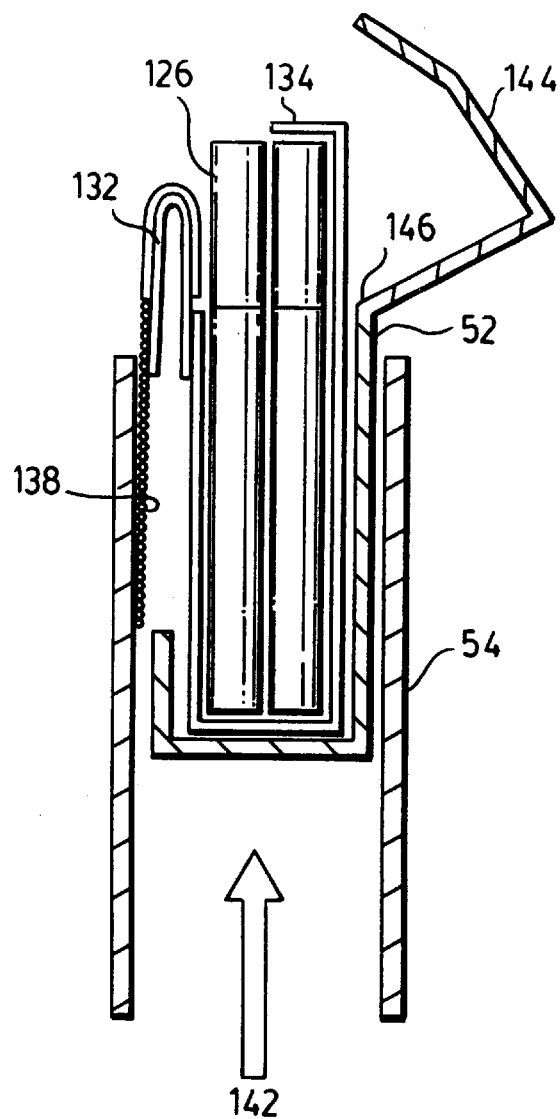
FIG.13a.
FIG.13b.

CIGARETTE OR TOBACCO PACKAGE WITH RE-USABLE AROMA RELEASANT FOR MULTIPLE PACKAGE OPENINGS

SCOPE OF THE INVENTION

A re-usable aroma releasant is provided on a package of cigarettes or a tobacco package such as pouch package or fine cut tobacco container. The aroma releasant is activated to release aroma every time the package is opened. The aroma releasant may be in the form of a reservoir where the flavour or aroma is released every time the reservoir is activated. This may be achieved by unsealing and resealing the reservoir every time the package is opened and closed. This system provides the user with a pleasant aroma associated with the use of tobacco and the flavour of cigarette smoking. The aroma releasant is in some way activated by the mechanical movement of opening the package to release the desired aroma. Conversely, when the package is closed such mechanical movement is translated into de-activating the aroma releasant. This provides for a re-usable aroma releasant where every time the customer opens the package, fresh aroma is released. The life of the aroma releasant is designed to suit the product life cycle of the package. The aroma may be released by an aromatic substance containing the essence of tobacco, coffee, menthol, or other pleasant aroma associated with the smoking of tobacco.

BACKGROUND OF THE INVENTION

Various flavourants have been incorporated in tobaccos, loose tobacco, cigarette tobacco and the like. Sometimes customers incorporate flavourants in the tobacco to maintain a desired freshness and aroma. Menthol has been incorporated in tobacco to provide a menthol feel when inhaling cigarette smoke. A smoker would understandably prefer to be reminded of the freshness of the cigarettes not only when the package is opened, but each time after the package is opened. This can be achieved to some extent when the cigarettes of a package are smoked reasonably quickly. There is not sufficient time for the cigarettes to dry out so that each time the package is opened the aroma of fresh cigarettes is released. It would be beneficial, however, to provide a release of aroma not only when the cigarette packages or tobacco packages are first opened but as well each subsequent multiple occurrence of such opening.

U.S. Pat. 4,717,017 describes a means for releasing an aromatic substance on opening of the package but that system is a one time use. The flavourant or aromatic substance is contained in a receptacle which is ruptured when the cigarette package is opened. Such rupturing of the receptacle releases the flavourant and hence, provides the customer with an aromatic smell when the package is first opened. Such rupturing of the receptacle prevents its re-use and as well can release flavourant into the tobacco which can affect the smokers' desired taste and flavour of the tobacco when smoked. Similar systems are described in U.S. Pat. Nos. 4,720,423 and 5,249,676. Again, each system is a one time use.

Resealable package closures are described in U.S. Pat. 5,333,729 for a variety of package designs. Resealable fragrance systems are described in U.S. Pat. 3,685,734 for use in providing a perfume, fungicide, herbicide, insecticide, algicide, fertilizer, medicament, anesthetic, corrosion inhibitor, food fragrance and animal repellent or attractant.

SUMMARY OF THE INVENTION

In accordance with this invention, a re-usable aroma releasant is provided on a cigarette package or other form of tobacco package which releases a pleasing aroma each time the package is opened. Correspondingly, when the package is closed the aroma releasant is deactivated.

In accordance with an aspect of the invention, the aroma releasant is provided on a cigarette or tobacco package such that mechanical movement of the package to the opened position opens the aroma releasant by removing a cover from an aromatic strip. Such opening releases the aroma to be smelled by the customer. Correspondingly, upon closing of the package, the mechanical movement is translated by an appropriate means to reseal the aroma releasant to block further release of aroma.

According to an aspect of the invention, a package for a tobacco product having a re-usable, resealable, aroma releasant, the packing comprises:

i) a tobacco product containment portion;

ii) a tobacco product containment closure portion; wherein the closure portion is removed from the containment portion to gain access to a tobacco product, iii) the aroma releasant having a peel seal connecting the containment portion and the closure portion, the peel seal sealing aroma in a substrate reservoir provided on the package, the peel seal being peeled from the substrate reservoir to permit opening the package and simultaneously release aroma from the substrate reservoir and correspondingly upon closure of the package, the peel seal being resealed over the substrate reservoir.

BRIEF DESCRIPTION OF THE DRAWINGS

Preferred embodiments of the invention are shown in the drawings wherein:

FIGS. 1a and 1b are perspective views of a laube cigarette box with a hinged lid on which an aroma strip is provided.

FIGS. 2a and 2b are perspective views of a hinged lid cigarette box with an aroma strip.

FIGS. 3a and 3b are perspective views of a shell and slide cigarette package with aroma strip.

FIG. 4 is a perspective view of a laube box in the open position.

FIGS. 5a and 5b are perspective views of the laube box of FIG. 4 in which foil sealed cigarettes are placed and on which an aroma strip is provided.

FIGS. 6a and 6b are perspective views of a laube box sealed with an aroma strip.

FIGS. 13a and 13b are sections through a shell and slide cigarette package showing automatic activation and deactivation of an aroma strip.

DETAILED DESCRIPTION OF A PREFERRED EMBODIMENTS

Figure 7A:
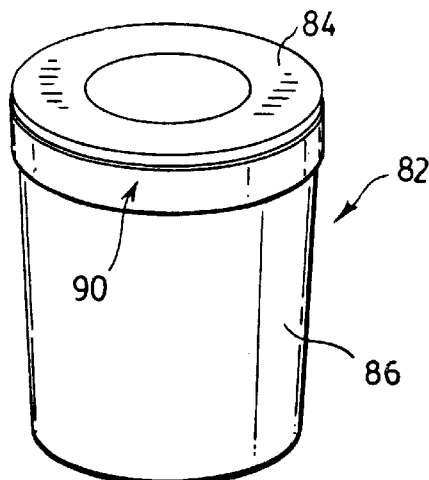
FIGS. 7a and 7b are perspective views of a fine cut tobacco container having an aroma strip as part of the lid seal.

The aroma releasant of this invention is provided on a package for a tobacco product such as a cigarette package, fine cut tobacco container or tobacco pouch. In order to achieve access to the cigarettes or tobacco, the aroma releasant must be activated either before or during the opening process. The aroma releasant, when activated, releases a pleasant aroma or flavour so that the customer experiences a very pleasant smell sensation which is designed to enhance the smoking experience each time the package, container or pouch is opened. The aroma releasant refers to any type of device which has the capability of being activated several times associated with each opening of the cigarette or tobacco package to release on those several occasions approximately the same intensity of aroma or flavour. The aroma releasant must be capable of containing a variety of different aromas such as the essence of aromatic tobaccos, rich tobaccos, coffee, menthol, chocolate and the like.

The aroma releasant may comprise an absorbent as the substrate in which the flavourant or source of aroma is stored and is released only when the cover to the absorbent is opened. The absorbent acts as a reservoir to retain the flavourant where the absorbent releases the volatiles of the flavourant each time it is exposed upon cigarette or tobacco package opening. The aroma releasant may be the commercially popular form of aroma strip which is covered with resealable film such as described in U.S. Pat. 3,685,734. Each time the film is pulled back from the strip, the strip releases the aroma of the volatile flavourant and the releasant is deactivated by applying the film back onto the strip. Preferably the film has a resealable, pressure sensitive adhesive to ensure that the strip is resealed upon each package closure. The aroma releasant is capable of being deactivated in one form or another to ensure that the released aroma, during cigarette package opening, is not released during package closure to ensure that the aroma does not pervade the cigarette or tobacco and affect its smoking taste and flavour.

With reference to the drawings various embodiments for the aroma releasant are shown in conjunction with various types of tobacco product packages for cigarettes, fine cut tobacco and pipe tobacco. In FIGS. 1a and 1b a standard laube cigarette package 10 is shown. The laube package 10 has a hard sided box base 12 which can be considered as a tobacco product containment portion and hinged lid 14 which can be considered as the tobacco product containment closure portion. The box has a cavity 16 in which foil sealed cigarettes are placed. The hinged portion 18 may be a connective paper between the lid 14 and the box base 12. On the end 20 of the box opposite the hinge 18 an aroma releasant may be provided in the form of an aroma strip which has pressure sensitive adhesive and which must be peeled back before the box can be opened to the position shown in FIG. 1b. The aroma strip 22 has a film seal or tear seal 24 which seals an aroma reservoir or substrate 26 provided on the box base 12. Every time the package 10 is opened, the film or peel seal 24 is peeled back to expose the reservoir 26 and allow the volatile flavourant in the form of an aroma to rise from the package. After the cigarette is withdrawn from the package, the package is closed and the strip 24 attached to the lid 14 with the pressure sensitive adhesive on its back surface 28 is applied over the flavourant reservoir 26 to reseal it and thereby deactivate the aroma release until the next opportunity when the package is reopened.

Similar aroma strips are provided on other package systems of FIGS. 2 and 3 having different styles of cigarette containment and closures therefor. In FIG. 2 a hinged lid cigarette box 30 has a cigarette container 32 and a hinged lid 34. The aroma strip 36 has the removable seal 38 covering the flavourant reservoir 40 provided on the box 32.. The strip 38 provided on the lid 34 has on its back face 42 a pressure sensitive adhesive. The strip 38 is peeled back to permit opening of the lid 34 thereby exposing the reservoir 40 of flavourant to release aroma when the package is opened. When the package is closed the sealing film 38 is pressed against the reservoir 40 to reseal it and prevent release of aroma until the next time the package is opened. With the aroma strip 44 of FIG. 3a the shell and slide package 46 is opened by peeling back the seal strip 48 to expose the flavourant reservoir 50 on the shell 54. This allows one to then open the package 46 by moving the slide 52 out of the shell 54. During the process a pleasing aroma is emitted from the reservoir 50. When the package is closed the strip 48 with pressure sensitive adhesive 56 on its back face is reapplied to the reservoir 50 to seal it off.

An alternative arrangement for the aroma strip is shown in FIGS. 4 and 5. The empty laube package 10 has a cavity 16 for receiving a foil sealed bundle of cigarettes 58. The foil sealed bundle 58 may be kept closed by the aroma strip 60 which as shown in Figure 5b is the usual tear seal 62 with pressure sensitive adhesive on its back face 64. The seal 62 covers the aroma reservoir 66. When the lid 14 is moved to the open position, one simply grasps the seal 62 and peels it back to expose the reservoir 66 provided on the foil wrap and thereby release a pleasing aroma as the foil lid portion 68 is also moved back to expose and allow access to one or more of the cigarettes 70 provided in the foil wrap. When the package is reclosed the seal 62 with the pressure sensitive adhesive is pressed onto the reservoir 66 to seal off the reservoir. The package is then closed by positioning the lid 14 on the box base 12. The seal 62 overlays the reservoir 66 such that when the foil flap 68 is pulled back to the overlying position the reservoir 66 is sealed off by the pressure sensitive adhesive seal. This ensures that the flavourant in the reservoir 66 does not travel or migrate into the cigarette 70 so that the smoker realizes the usual expected flavourant taste when smoking the cigarette 70.

An alternative arrangement for the aroma strip is shown in FIG. 6. The laube package 10 with its parting line 72 which defines the separation between the lid 14 and the base 12 may rely on the aroma strip 74 to act as the closure seal for the package. The base 12 may include an aroma reservoir 76 which is covered by the peelable strip 78 having pressure sensitive adhesive on its back face 80. With the laube box 10 in its closed position, the strip covers the reservoir 76. In order to open the box 10 the strip 78 is peeled back to expose the flavour reservoir 76 and thereby release the volatile aroma of desired flavour. Again, when the package is closed, the strip 78 is applied over the reservoir to seal it off until the next time the package is opened.

Figure 7B:
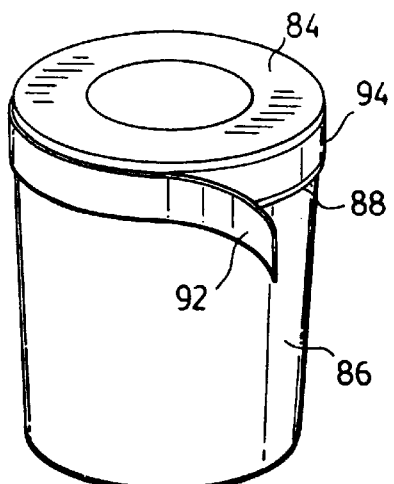
Figure 8A:
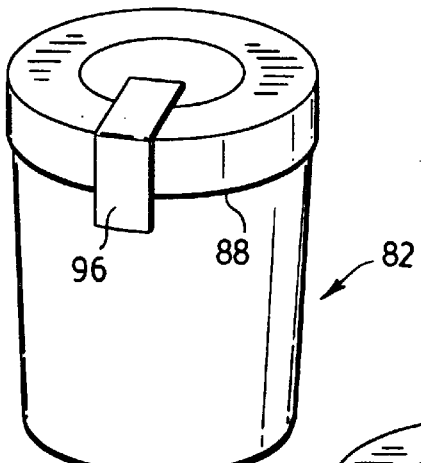
FIGS. 8a and 8b are perspective views of a fine cut tobacco container having an aroma strip as part of the lid seal.
Figure 8B:
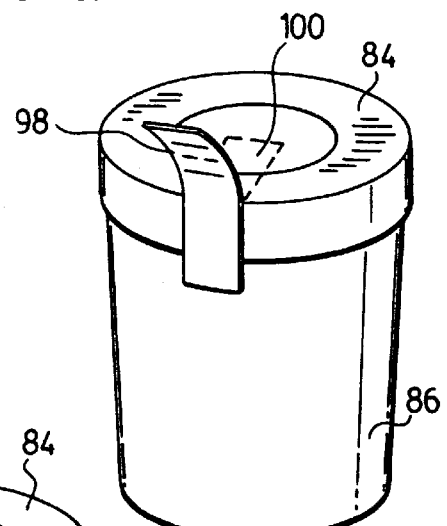
Figure 9:
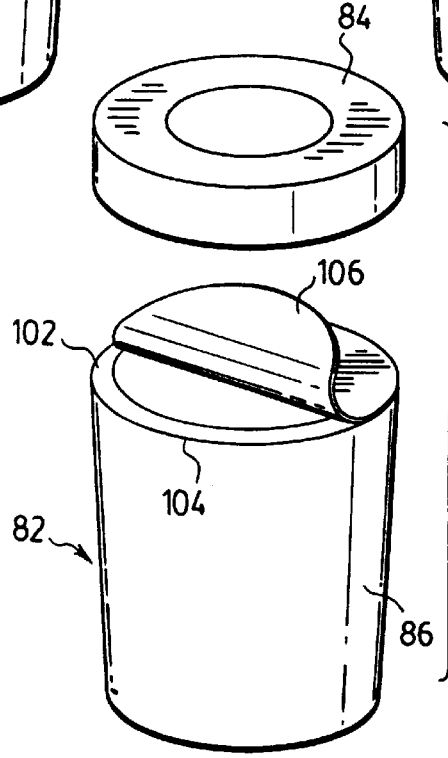
FIG. 9 is a perspective view of an open fine cut tobacco container where an aroma strip is part of the foil seal for the container tub.

In FIGS. 7,8 and 9 various aroma strips are shown for fine cut tobacco contained in tobacco canisters. In FIGS. 7a and 7b the tobacco canister 82 has a lid 84 and tub 86. The lid separates from the tub at parting line 88. The aroma strip 90 is positioned over the parting line 88. In order to remove lid 84 from the tub 86 the film seal 92 is pulled back to expose the aroma reservoir 94 provided on the lid 84 although it is understood that the reservoir may be provided on the container in this and other embodiments of this invention. The volatile aroma is released from the flavourant in the reservoir 94 so that when the canister is opened the customer realizes the desired smell. When the canister is closed the reservoir 94 is resealed by lightly applying the strip 92 to the reservoir where pressure sensitive adhesive holds the seal in place. Alternatively, with the canister 82 of FIG. 8, the aroma strip 96 may extend transversely of the parting line 88, rather than longitudinally therewith. As with FIG. 7, the aroma strip 96 has a seal 98 which may be pulled back to expose the aroma reservoir 100 provided on the lid 84. One may then open the container with the desired aroma released. When the lid is reapplied to the tub 86, the strip 98 with pressure sensitive adhesive is applied back over the aroma reservoir 100 to stop escape of the volatile aroma. It is appreciated that the lid 84 is threaded onto the tub 86 in a manner such that the aroma reservoir 100 is always in register with the strip 98 when the lid is rotated to the closed position. The canister 82 of FIG. 9 may have on the tub 86 an aroma reservoir 102 about the rim portion. The reservoir 102 is covered by re-usable seal 106. As with the package 105, the seal 106 closes off the reservoir 102 when the canister is closed to ensure that none of the aroma permeates the tobacco and affects its flavour and taste when smoked.

Figure 10:
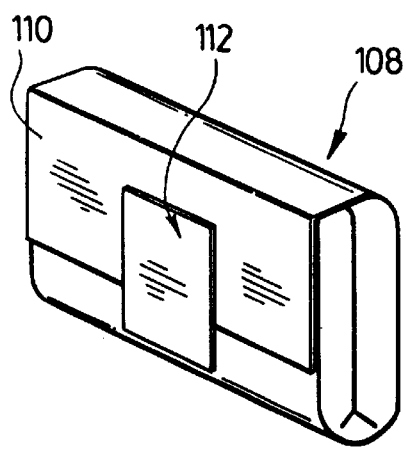
FIG. 10 is a perspective view of a tobacco pouch in the closed position.
Figure 11:
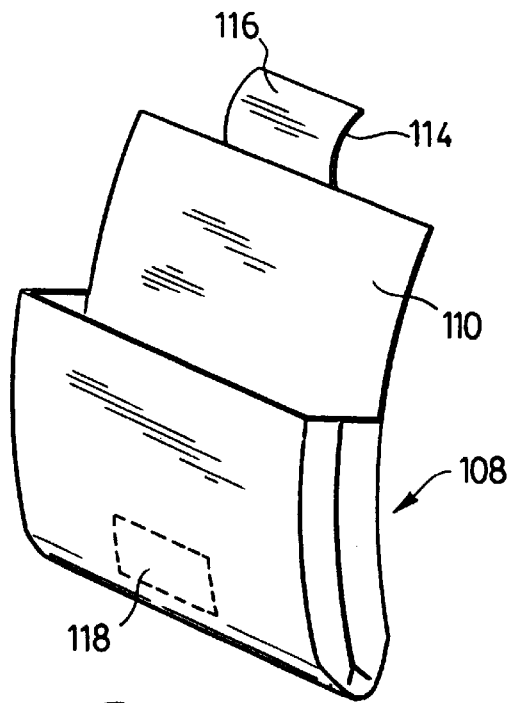
FIGS. 11 and 12 are perspective views of tobacco pouches in the open positions having various placements of aroma strips.
Figure 12:
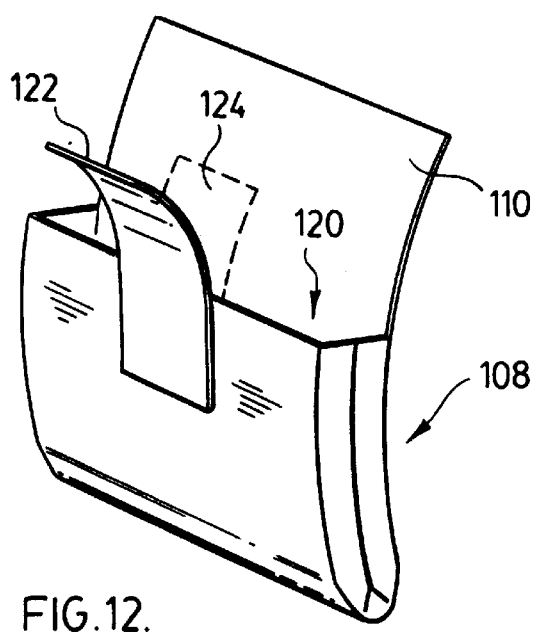

Two alternatives for fine cut tobacco pouch or pipe tobacco pouch are shown in FIGS. 10, 11 and 12. The pouch 108 has the overlapped pouch closure or flap 110. The closure is held in place by an aroma strip 112. The strip 112 is opened by peeling back the film seal 114 which has pressure sensitive adhesive on its underside 116. The seal 114 overlays the aroma reservoir 118 provided on the pouch. When the pouch 108 is opened by pulling back the flap 110 a pleasing aroma is released from the reservoir 118. When the pouch is reclosed and the seal strip 114 applied over the reservoir 118, the release of aroma is deactivated until the next opening. Similarly with the pouch 108 of FIG. 12, when the flap 110 is pulled to the open position access to within the cavity 120 is permitted when the seal 122 is pulled away from the flavourant reservoir 124. This allows access to the tobacco within the cavity 120. After the desired amount of tobacco is removed, the seal 122 is reapplied to the reservoir 124 to seal it off and the flap 110 closed. The reservoir 124 is positioned so that the seal with the pressure sensitive adhesive completely seals the reservoir to preclude aroma permeating tobacco within the pouch 108.

It is of course appreciated that it is not absolutely essential that the reservoir be completely sealed off if the flavourant in the reservoir is complimentary to or the same as the desired aroma in the tobacco. For example, with menthol flavoured tobaccos or aromatic tobaccos, if the flavourant is the same then some leakage from the reservoir into the tobacco is considered to be complimentary to the tobacco flavour. However, if for example, the flavourant were chocolate then it would be desirable to seal off the reservoir to prevent the chocolate flavour permeating the tobacco and thereby affecting its taste when smoked.

It may be desirable to automate the activation and deactivation of the aroma strip. An exemplary embodiment of this automation is shown in FIGS. 13a and 13b in respect of a standard shell and slide package 46 of FIG. 3 only modified in the manner shown. The slide 52 is contained within the shell 54. A bundle of cigarettes 126 is contained in the usual foil seal or barrier material 128. The aroma strip 130 in the form of a flap 132 secures the foil closed. The seal 132 covers the flavour reservoir 134. The strip 132 is connected to the interior 136 of the shell 54 by a flexible link 138 which in turn is fastened to the seal 132 at 140. When the package 46 is opened by moving the slide in direction of arrow 142, the flexible link 138 pulls the seal 132 away from the reservoir 134 to expose the cigarettes 126. As this happens, the aroma is released from the reservoir 134 where the slide flap 144 is in the open position as hinged about line 146. After withdrawal of a cigarette from the bundle, the slide is pushed back down into the shell 54 where the seal 132 tracks upwardly over the cigarette bundle and as the lid 144 is brought down onto the seal 132, it is compressed against the reservoir 134 to reseal the reservoir and prevent release of flavourant until the package is reopened.

It is apparent from the detailed description of the various embodiments of this invention that a re-usable aroma releasant functions very well in combination with various cigarette and tobacco containers and packages to provide on a repetitive, consistent basis, an aroma release which provides the customer with the desired fresh or pleasing scent each time the package is opened. The aroma reservoir is designed to produce sufficient volatiles to match the product life cycle which may be 1 to 2 days for a package of cigarettes, 3 to 4 days for a pouch of tobacco, and 7 to 8 days for fine cut tobacco containers.

Although various preferred embodiments of the invention have been described here in detail it will be appreciated by those skilled in the art that other alternatives of the invention are contemplated without departing from the spirit of the invention or the scope of the appended claims.

We claim:

1. A package for a tobacco product having a re-usable, resealable, aroma releasant, said packing comprising:
   i) a tobacco product containment portion;
   ii) a tobacco product containment closure portion; wherein said closure portion is removed from said containment portion to gain access to a tobacco product;
   iii) said aroma releasant having a peel seal connecting said containment portion and said closure portion, said peel seal sealing aroma in a substrate reservoir provided on said package, said peel seal adapted to be peeled from said substrate reservoir to permit opening said package and simultaneously release aroma from said substrate reservoir and correspondingly upon closure of said package, said peel seal adapted to be resealed over said substrate reservoir.

2. A package of claim 1 for containing cigarettes, said package being a hinged lid cigarette box wherein:
   i) said containment portion is a box;
   ii) said closure portion is a hinged lid interconnected to said box;
   iii) said substrate reservoir being provided on said box and said peel seal being provided on said lid to overlap and seal said reservoir when said lid is in a closed position.

3. A package of claim 1 for containing cigarettes, said package being a shell and slide package wherein:
   i) said containment portion is a slide;
   ii) said closure portion is a shell;
   iii) said substrate reservoir being provided on said shell and said peel seal being provided on said slide to overlap and seal said reservoir when said slide is in a closed position.

4. A package of claim 1 for packaging cigarettes, said package being a laube package wherein:
   i) said containment portion is a base;
   ii) said closure portion is a lid hinged to said base;
   iii) said substrate reservoir being provided on said base and said peel seal being provided on said lid to overlap and seal said reservoir when said lid is in a closed position.

5. A package of claim 1 for packaging cigarettes, said package being a laube package wherein:
   i) said containment portion is a foil wrap;

ii) said closure portion is a portion of said foil laid over a front portion of said foil wrap;

iii) said substrate reservoir being provided on said foil wrap adjacent said foil portion and said peel seal being provided on said foil portion to overlap and seal said reservoir when said foil portion closes said foil wrap.

6. A package of claim 1 for packaging cigarettes, said package being a shell and slide package having an automatic opening and closure for said aroma releasant, wherein:

i) said containment portion is formed of barrier material housed in a slide;

ii) said closure portion is a barrier flap which opens from barrier top and down along a barrier side;

iii) said substrate reservoir being provided on barrier top adjacent said flap and said peel seal being provided on said barrier flap to overlap and seal said reservoir when said barrier flap is in a closed position;

iv) link means for connecting said peel seal to said shell whereby sliding said slide out of said shell pulls said peel seal off said reservoir and opens said flap and subsequently sliding said slide into said shell closes said flap and reseals said reservoir.

7. A package of claim 1 for containing fine cut tobacco wherein:

i) said containment portion is a pouch having an access opening;

ii) said closure portion is a flap connected to said pouch and which closes said pouch opening;

iii) said substrate reservoir being provided on said pouch adjacent a flap edge when said flap is in a closed position and said peel seal is provided on said flap to overlap and seal said reservoir when said lid is in a closed position.

8. A package of claim 1 for containing fine cut tobacco wherein:

i) said containment portion is a pouch having an access opening;

ii) said closure portion is a flap connected to said pouch and which closes said pouch opening;

iii) said substrate reservoir being provided on an interior portion of said flap and said peel seal being provided on said pouch adjacent said access opening to overlap and seal said reservoir prior to said flap being folded over to close said pouch opening.

9. A package of claim 1 for containing fine cut tobacco wherein:

i) said containment portion is a container;

ii) said closure portion is a lid for closing an open top of said container;

iii) said peel seal being peeled from said reservoir when said lid is removed from said container and fine cut tobacco is accessed through said container open top.

10. A package of claim 9 wherein said substrate reservoir is provided on said container and said peel seal is provided on said lid to overlap and seal said reservoir when said lid is in a closed position.

11. A package of claim 9 wherein said substrate reservoir is provided on said lid and said peel seal is provided on said container to overlap and seal said reservoir when said lid is in a closed position.

12. A package of claim 9 wherein said substrate reservoir is provided on container rim and said peel seal is provided on a barrier foil for sealing said container open top, said peel seal on said barrier foil sealing said reservoir when said barrier is positioned on said container top.

13. The package of claim 1 wherein mechanical movement of the package to an opened position removes said peel seal thereby activating said aroma releasant and wherein mechanical movement to a closed position deactivates the aroma releasant.

14. A package of claim 13 wherein said aroma releasant comprises an absorbent in which a flavourant or source of aroma is stored and is only released when said peel seal is removed to activate said aroma releasant.

15. The package of claim 14 wherein said absorbent comprises a reservoir to retain said flavourant when said aroma releasant is deactivated.

16. The package of claim 14, wherein said aroma releasant releases aroma or flavour each time said peel seal is removed.

17. The package of claim 15 wherein said absorbent releases volatiles of the flavourant each time it is exposed by removal of said peel seal.

18. The package of claim 17 wherein said aroma releasant is an aroma strip covered with resealable film.

19. The package of claim 18 wherein said film has a pressure sensitive adhesive and wherein said aroma strip is resealed each time said package is closed.

* * * * *